United States Patent [19]

Kelly et al.

[11] Patent Number: 4,710,031
[45] Date of Patent: Dec. 1, 1987

[54] MICROTITER PLATE READER

[75] Inventors: John E. Kelly, Duluth, Ga.; Don C. Jones, Madison, Wis.; Frederick R. Tuck, Norcross; William A. Zimmermann, Lilburn, both of Ga.; Kenneth R. Clark, Cottage Grove, Wis.

[73] Assignee: Lancraft, Inc., Norcross, Ga.

[21] Appl. No.: 761,199

[22] Filed: Jul. 31, 1985

[51] Int. Cl.⁴ ............................................. G01N 21/00
[52] U.S. Cl. ..................................... 356/440; 356/432; 356/244
[58] Field of Search ................. 436/809; 356/357, 432, 356/436, 440, 441, 244; 422/68, 73

[56] References Cited

U.S. PATENT DOCUMENTS

| | | | |
|---|---|---|---|
| 2,342,409 | 8/1940 | Levy | 436/511 |
| 3,652,169 | 3/1972 | Danti et al. | 356/244 |
| 3,712,746 | 1/1973 | Bergeron | 356/432 |
| 3,773,426 | 11/1973 | Mudd | 356/434 |
| 4,099,881 | 7/1978 | Vanden Broek et al. | 356/244 |
| 4,221,867 | 9/1980 | McFadden | 356/244 |
| 4,358,203 | 11/1982 | Citrin | 356/432 |
| 4,457,894 | 7/1984 | Clark et al. | 422/73 |

Primary Examiner—R. A. Rosenberger
Assistant Examiner—Crystal D. Cooper
Attorney, Agent, or Firm—Isaksen, Lathrop, Esch, Hart & Clark

[57] ABSTRACT

A microtiter plate reader is disclosed which allows visual examination of the contents of the wells of a microtiter plate having an array of wells. The microtiter plate reader includes supporting means for supporting the microtiter plate with the wells opening generally upwardly and a light emitting surface is adapted to extend under a microtiter plate so held. Regions of reduced light emission on the light emitting surface are arranged in an array corresponding in relative position to a selected portion of the array of microtiter plate wells. Locator means are provided for locating the microtiter plate with respect to the array of regions of reduced light emission to allow selective alignment of the wells with the dark regions, providing a dark background to the bottom of the wells which are then illuminated indirectly. The wells can be illuminated directly when the dark regions are out of alignment with the wells.

13 Claims, 5 Drawing Figures

MICROTITER PLATE READER

TECHNICAL FIELD

The present invention relates to devices for optically examining containers of bacterial growth media to detect the presence or absence of bacterial growth therein and, in particular, for examining the multiple wells of a conventional microtiter plate.

BACKGROUND ART

In various contexts, it is required that substantially clear media or sample containers be examined for the presence of a precipitate, bacterial growth, or the like. Many devices exist to aid in this process. Generally the clear media or sample containers are illuminated from the side by a light source so shielded as to not be observable directly from the viewer's location. The clear media or a sample container so side lighted is then viewed against a dark background with the result that light scattered toward the viewer by suspended material may be seen more easily. Examples of such devices include Levy, U.S. Pat. No. 2,342,409; Danti, et al., U.S. Pat. No. 3,652,169; Bergeron, U.S. Pat. No. 3,712,746; Vanden Broek, et al., U.S. Pat. No. 4,099,881; and Clark, et al., U.S. Pat. No. 4,457,894. McFadden, U.S. Pat. No. 4,221,867 is such a viewer specifically adapted for use with microtiter plates having rows of wells, each of which wells contains a sample to be viewed. McFadden shows an array of vanes or baffles so situated relative to each other that an entire row of wells may be viewed from above simultaneously while being lit from two sides.

It is often necessary in certain procedures that the wells of a microtiter plate be examined first in such a way that suspended material or small buttons of precipitate may easily be seen and then in such a way that the colors of the media in each well can be evaluated. Side lighting against a dark background is useful for the first type of examination but is inadequate for the second. In addition, it is an advantage to be able to examine a large number of such wells at the same time without the need to move the microtiter plate. Thus, it is sometimes desirable to be able to examine a block or other array of such wells and to change with facility between alternate viewing modes in which the wells of a plate are examined both for color and the presence of bacterial growth as evinced by turbidity, a precipitate, or the like.

SUMMARY OF THE INVENTION

The microtiter plate reader of the invention enables the efficient visual examination of the contents of the wells of a microtiter plate having an array of wells. The microtiter plate is supported by the reader during examination with the wells in the plate opening generally upwardly. A light emitting surface is provided under a microtiter plate held by the supporting means of the reader. The light emitting surface has an array of regions of reduced light emission corresponding in relative position to a selected portion of the array of microtiter plate wells. Locator means are provided for locating the microtiter plate in selected relation to the array of regions of reduced light emission to selectively align the wells therewith.

A method for optically examining the contents of the wells of a microtiter plate includes the step of placing the microtiter plate on a light emitting surface having an array of regions of reduced light emission, the array of such regions being alignable with a portion of the array of the wells of the microtiter plate to provide a dark background behind the wells. The method further includes aligning the microtiter plate with the array of regions of reduced light emission so that the wells are observable against the dark background provided by the regions of reduced light emission while the contents of the wells are illuminated by light from the light emitting surface impinging on the wells from a generally sideward direction.

A primary object of the invention is to provide means for conveniently examining the contents of the wells of a microtiter plate having an array of such wells.

A second object of the invention is to provide in particular for a means by which the contents of the wells may be illuminated by light impinging on them substantially from the side and preferably from all sides.

Another object of the invention is to provide such a device in which the wells of the microtiter plate may alternatively be viewed against a light emitting surface such that light impinges on the wells immediately from beneath.

A further object of the invention is to provide such a device in which a large portion and even all of the wells of the microtiter plate may be viewed at the same time.

Yet another object of the invention is to provide such a microtiter plate reader in which selected zones of the microtiter plate may be delineated or otherwise set off by visually apparent indicia.

Yet another object of the invention is to provide some or all of the features referred to above as part of a physically simple device that is relatively inexpensive to manufacture and maintain.

Other objects, features, and advantages of the invention will be apparent from the following detailed description taken in conjunction with the accompanying drawings showing a preferred embodiment of a microtiter plate reader exemplifying the principles of the invention.

DESCRIPTION OF THE PREFERRED EMBODIMENT

Figure 1:
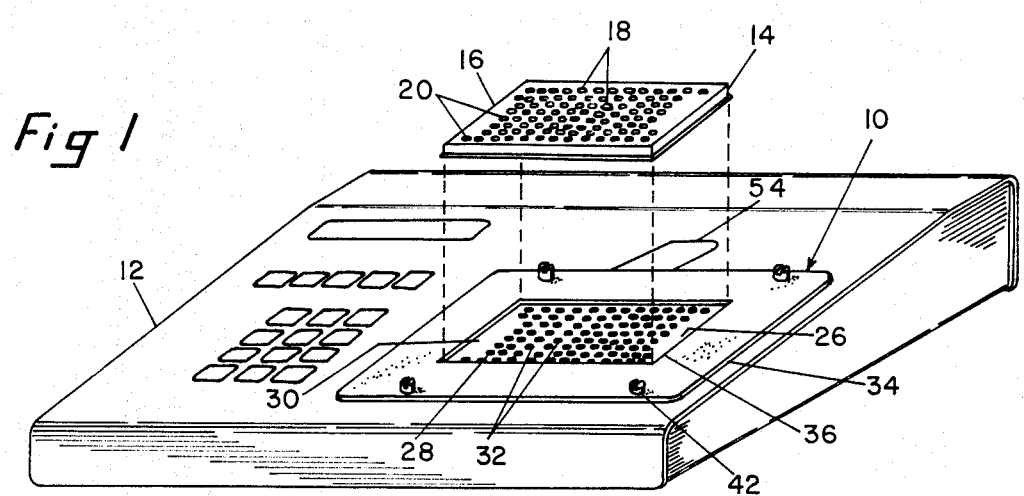
FIG. 1 is a perspective view of the preferred embodiment of the microtiter plate reader of the invention, incorporated within a laboratory instrument, with a microtiter plate shown in exploded relation thereto.

Referring more particularly to the drawings, wherein like numbers refer to like parts, FIG. 1 shows a microtiter plate reader, generally indicated at 10, constructed in accord with the present invention and incorporated within a laboratory instrument, indicated at 12. The microtiter plate reader 10 is adapted for use with a conventional microtiter plate 14. Conventional microtiter plates 14 typically have a rectangular body 16 that contains a multiplicity of upwardly opening wells 18. The wells 18 are arranged in standardized arrays and usually in elongated rows extending from side to side across the body 16, such as the rows shown in the figures at 20. Thus, a typical array of wells 18 on a microtiter plate 14 includes a plurality of rows 20 extending from side to side across the microtiter plate, each row separated from the rows adjacent to it by a selected space, such as the space indicated by the bracket at 22 of FIGS. 4 and 5.

The microtiter plate reader 10 of the invention is adapted for use with such a microtiter plate 14. The microtiter plate reader 10 includes a supporting means for supporting the microtiter plate 14 with the wells 18 opening upwardly. The microtiter plate reader 10 further includes a light emitting surface 26 that is presented generally upwardly and preferably is substantially planar. The light emitting surface 26 may itself serve as the supporting means, although a frame surrounding the light emitting surface, a rack, or any functionally equivalent structure could be used instead. As discussed further below, with certain types of microtiter plates, the best indirect illumination of the wells is obtained if the plate is supported off of the light emitting surface. All such alternative embodiments are within the scope and spirit of the invention. The light emitting surface 26 has regions of reduced light emission 28 arranged in an array adapted to be alignable with a selected number of the wells 18 of the microtiter plate 14 when the microtiter plate is supported by the supporting means. In the preferred embodiment, the microtiter plate reader 10 includes a transparent overlay 30 having opaque and preferably black dots 32 arrayed as a black dot array 33. The transparent overlay 30 is adapted to be placed over the light emitting surface 26 in sliding relation thereto, the black dots 32 providing the regions of reduced light emission 28 referred to above.

Locator means are provided for locating a microtiter plate 14 in a selected, easily maintained relation to the regions 28 of reduced light emission. Preferably the locator means includes a bezel 34 having a window 36 adapted to contain the microtiter plate 14. The bezel 34 extends over the light emitting surface 26, so that a microtiter plate 14 placed within the window 36 is held on the light emitting surface 26 in easily maintained relation to the array of regions 28 of reduced light emission to selectively align the wells therewith. If a transparent overlay 30 is used, the bezel 34 preferably is spaced above the light emitting surface 26 sufficiently to allow the transparent overlay to slide freely, with the transparent overlay sandwiched between the light emitting surface 26 and the bezel 34, as is shown in the figures. Preferably the bezel 34 is attached to the remainder of the microtiter plate reader 10 by means of threaded posts 38 extending upwardly therefrom. The bezel 34 includes bezel holes 40 extending through the bezel and adapted to receive the upwardly extending threaded posts 38. Preferably the bezel holes 40 are made larger in diameter than the threaded posts 38, so that the bezel may be moved about the threaded posts to a selected extent. Fingernuts 42 are threadedly engaged on the threaded posts 38 and may be turned down thereon so as to contact the bezel 34, sandwiching it between the fingernuts and the remainder of the microtiter plate reader 10 to secure it in a selected location thereon.

A microtiter plate 14 to be read is held by the locating means over the light emitting surface 26 in such an orientation that at least some of the wells 18 of the microtiter plate are located directly over regions of reduced light emission. In the preferred embodiment described, the transparent overlay 30 is selected to have black dots 32 that correspond approximately in size to the wells 18, with one black dot for each well, and the black dot array 33 corresponds to the array of wells 18. The microtiter plate 14 is placed within the window 36 of the bezel 34 to be held thereby in easily maintained relation to the transparent overlay located beneath the bezel. Preferably the window 36 has opposing sides 44 and a top 46 and bottom 48. The size of the window 36 may be so selected that the microtiter plate 14 is held snugly within the opposing sides 44 and the top and bottom 46, 48. However, in the event the microtiter plate 14 is smaller than the window 36, it still may be held in selected relation to the black dot array 33 by being slid to a corner of the window, against a selected side 44 and either the top or bottom 46, 48. It is preferred in such a situation that the microtiter plate 14 is slid to the left bottom corner of the window 36. By loosening the fingernuts 42 and moving the bezel 34 within the limitation of the bezel holes 40, the exact location of a microtiter plate 14 held within the window 36 relative to the underlying black dot array 33 may be adjusted precisely. By this means, the array of wells 18 may be aligned precisely over the black dot array 33.

The regions 28 of reduced light emission, such as the black dots 32 of the transparent overlay 30, block the transmission of the light directly upwardly from the light emitting surface 26 to the eye of the user of the microtiter plate reader 10. Consequently, the contents of the wells 18 may be viewed against a dark field. Preferably the light emitting surface 26 emits light omnidirectionally, as is the case when the light emitting surface is a translucent material lit from behind. In such an event, a portion of the light emitted from the light emitting surface 26 immediately surrounding each region 28 of reduced light emission is directed at an angle to the light emitting surface, over the region of reduced light emission. This light provides side lighting for each of the wells 18 located over a region 28 of reduced light emission, illuminating the contents of the wells. Such side lighting is provided from all sides of each region 28 of reduced light emission. In the event a suspension or other light refracting or reflecting material is contained within a well 18, it appears as a relatively bright illuminated object or material against the dark background provided by the region 28 of reduced light emission. Thus, it is readily seen by the user of the microtiter plate reader 10.

Figure 4:
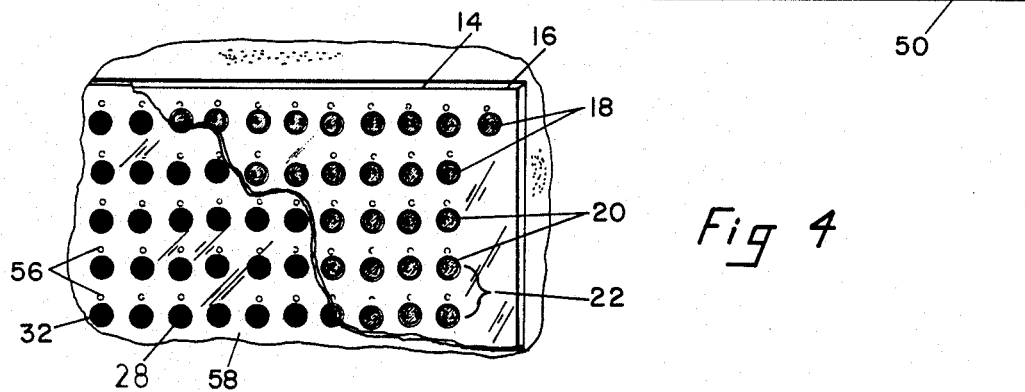
FIG. 4 is a broken away portion of the light emitting surface of the microtiter plate reader, shown from above, with a microtiter plate in place upon the light emitting surface and the black dot array in the dark field position.
Figure 5:
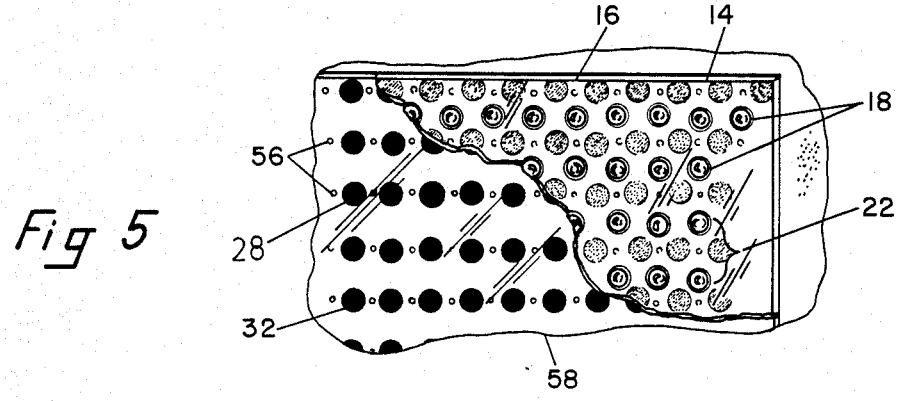
FIG. 5 is a view comparable to that of FIG. 4 but with a black dot array in the light field position.

In the preferred embodiment of the invention, shifting means are provided for shifting the relative location of the regions 28 of reduced light emission and the wells 18 of the microtiter plate 14, as the microtiter plate is held within the window 36 or equivalent locating means. The shifting means so shift the wells 18 relative to the regions 28 of reduced light emission that the wells are held over bright portions of the light emitting surface 26, with the regions of reduced light emission being interspersed between the wells. As a consequence, the wells 18 may be observed by a user of the microtiter plate reader 10 against a light field. Under such circumstances, the color of the contents of the wells 18 may be more easily evaluated than it can when the wells are observed against a dark field. Wells 18 held directly over a black dot 32 or comparable region 28 of reduced light emission shall be referred to as being in the "dark field position," as is shown in FIG. 4. Wells 18 held over a part of the light emitting surface 26 that is not reduced in light emission shall be referred to as being in the "light field position," as is shown in FIG. 5.

Figure 2:
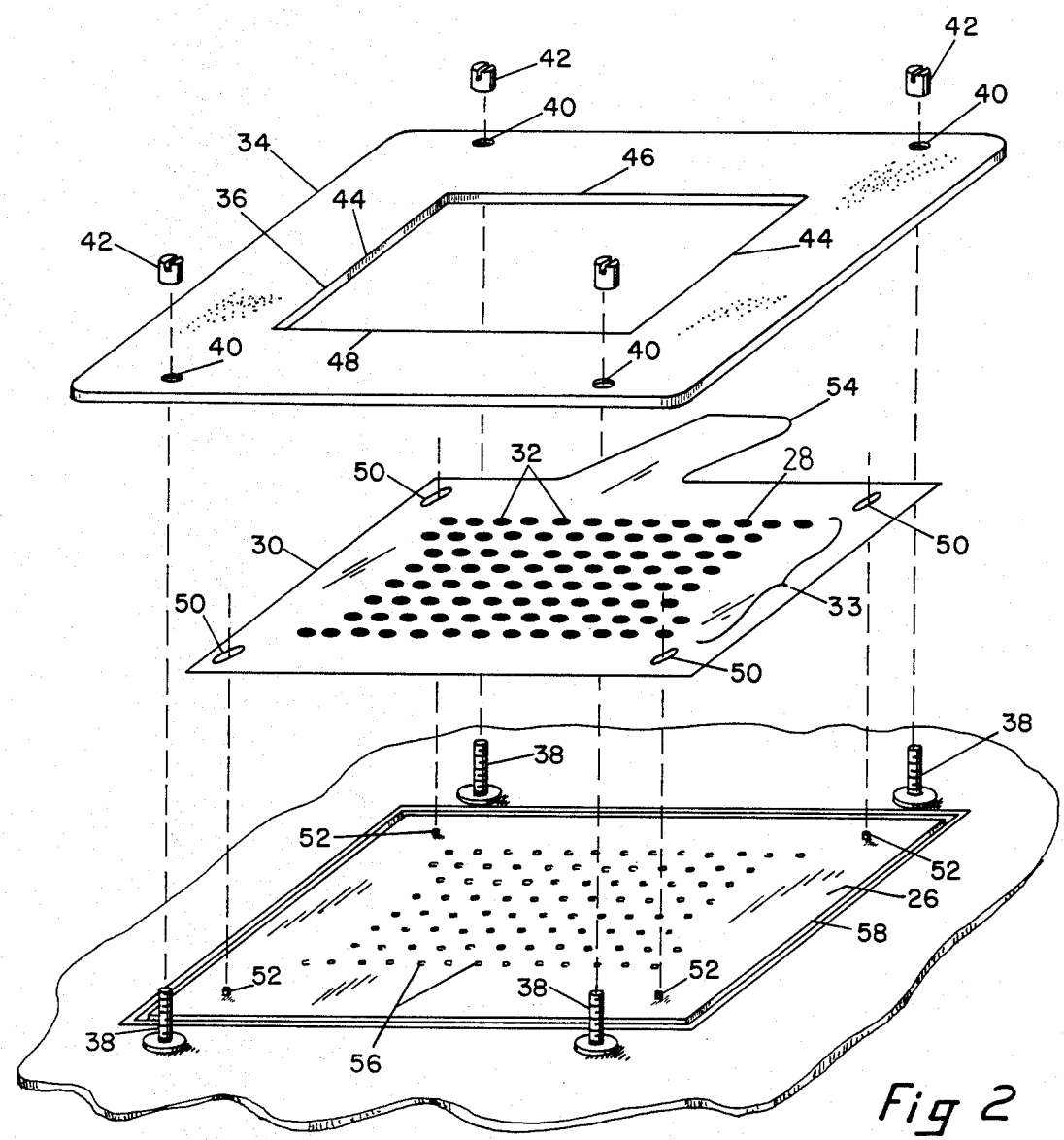
FIG. 2 is a perspective view of the microtiter plate reader of FIG. 1 with various parts shown in exploded relation.
Figure 3:
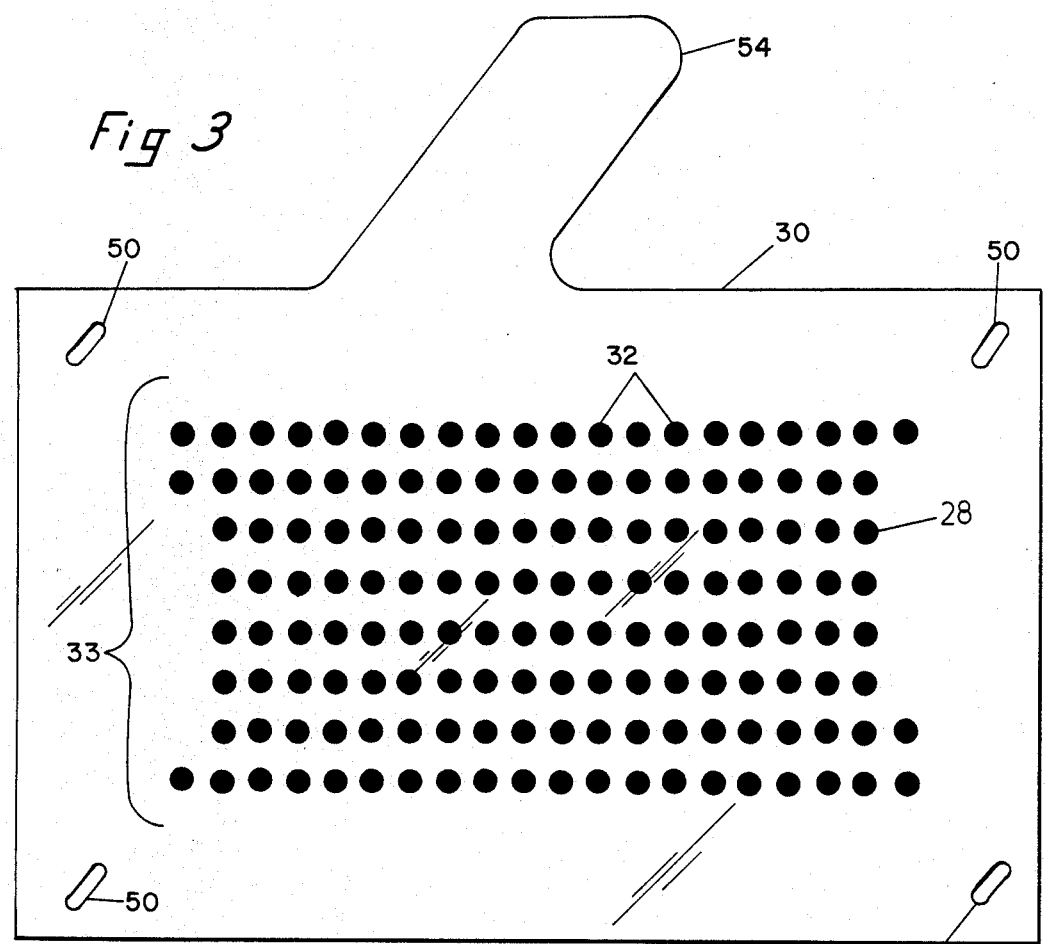
FIG. 3 is a top plan view of the transparent overlay of the microtiter plate reader of FIG. 1.

In the preferred embodiment of the microtiter plate reader 10 described above, the transparent overlay 30 bearing the black dot array 33 is adapted to slide relative to the bezel 34 in a controlled and specific way. The transparent overlay 30 includes a selected number of longitudinally extended guide slots 50. The longitudinal axes of the guide slots 50 are parallel to each other at a selected angle to the bottom 48 of the window 36, when the transparent overlay 30 is held in place beneath the bezel 34. Guide pins 52 extend upwardly in fixed relation to the threaded posts 38, preferably from the light emitting surface 26, as can be seen in FIG. 2. The guide pins 52 are adapted to receive the guide slots 50 in freely sliding relation, so that the transparent overlay 30 may be shifted freely for a limited distance in a direction parallel to the longitudinal axis of the guide slots. Preferably the transparent overlay 30 includes a tab 54 or other, equivalent means to manipulate the transparent overlay with convenience in order to move the transparent overlay within the limitations of movement imposed by the interaction of the guide slots 50 and guide pins 52.

With the transparent overlay 30 set in place on the light emitting surface 26 with the guide pins 52 extending through the guide slots 50 and the bezel 34 set in place on the threaded posts 38, the bezel is shifted until the black dots 32 of the transparent overlay are so oriented relative to the window 36 that they are aligned with the array of wells 18 of a microtiter plate 14 to be read when the transparent overlay is so moved that the guide pins 52 are at a first extreme end of the guide slots 50. The bezel 34 is then secured in place by tightening the fingernuts 42 thereagainst. The guide slots 50 have a length selected to be such that when the transparent overlay 30 is so moved that the guide pins 52 have been shifted to the other extreme end of the guide slots, the black dots 32 are moved relative to the rows 20 of wells 18 that they lie beneath the spaces 22 between the rows. Thus, by a simple movement of the transparent overlay 30, the wells 18 of a microtiter plate 14 may be viewed first in a dark field position, with side lighting and against a dark background, and then in a light field position, with the addition of direct lighting from beneath and against a light background. This facilitates the efficient reading of the wells 18 for a precipitate, turbidity, or the like followed by a comparably convenient reading of the wells for color.

The embodiment of the microtiter plate reader 10 just disclosed in which the microtiter plate 14 to be read is held in fixed relation to the bezel 34 over a stationary light emitting surface 26 while a transparent overlay 30 bearing a black dot array 33 is moved, clearly is only one possible embodiment of the invention. Thus, it would be possible to supply a light emitting surface 26 having a black dot array 33 or the like directly marked upon it. A bezel having a window, all corresponding generally to that just described above, could be provided with the window of the alternative embodiment having dimensions such that the wells 18 of the microtiter plate are in the dark field position when the microtiter plate is shifted to the far lower left corner of the window and in the light field position over portions of the light emitting surface unobstructed by black dots when the microtiter plate is shifted to the upper right hand corner of the window. The shift at an angle from lower left to upper right is especially convenient, whether accomplished by moving a transparent overlay 30 or by moving the microtiter plate 14 itself, as just described, because of the relative location and spacing of the wells 18 of conventional microtiter plates 14. Typically such wells 18 are sufficiently crowded together that movement of a black dot array 33 parallel to a row 20 of wells would not suffice to place the wells over a portion of the light emitting surface 26 unobstructed by the black dots. There would be insufficient room between the wells 18 to accommodate the dots 32. The same is true of movement at a right angle to the longitudinal axis of the rows 20. However, because conventional wells 18 are round, the preferred movement of the wells relative to the black dots 32 described above allows the wells to be oriented over a space between the black dots sufficiently large to allow the wells to be viewed against a light background. Clearly the preferred direction and extent of movement would differ for differing arrays of wells 18 and black dots 32.

It has been found that, with some types of microtiter plates, it is necessary to support the plate above the light emitting surface to obtain adequate indirect illumination of the wells. This support can be achieved by providing a lip or shelf on the inner sides of a raised bezel on which the edges of the plate can rest.

A transparent overlay 30, as described above, is preferred in part because such overlays are easily removed and exchanged for alternative transparent overlays having a different black dot array 33. Thus, a microtiter plate reader 10 can be easily and immediately converted for use with any of several designs of microtiter plates 14 having differing arrays of wells 18. In addition, the use of a transparent overlay 30 allows the dark regions 28 to be moved relative to the wells 18 without movement of the wells relative to the underlying light emitting surface 26. Consequently, the light emitting surface 26 may bear other marks or include other visual indicators for identifying individual wells 18 or groups of wells, the marks remaining in the same location relative to the wells as the wells are viewed in either dark or light field positions.

In the preferred embodiment of the microtiter plate reader 10 of the invention, the light emitting surface 26 includes indicator light holes 56 extending therethrough. The indicator light holes 56 may be so spaced on the light emitting surface 26 that an indicator light hole is located directly above each well 18 of a microtiter plate 14 when the microtiter plate is held in position within the window 36 of the bezel 34 in, for example, the lower left corner of the window. The indicator light holes may be illuminated from beneath by LED's or otherwise, creating a means for distinguishing one well from the next at a glance in accord with any of a number of possible uses. Preferably the light emitting surface 26 is the uppermost surface of a translucent plate 58, so that the indicator light holes 56 extending therethrough act as collimators such that light shining upwardly from beneath the translucent plate 58 is emitted from the indicator light holes 56 as a highly directional beam projecting at an angle approximately normal to the light emitting surface 26. Consequently, light emitted from the indicator light holes 56 may be observed by a user of the microtiter plate reader 10 without impinging upon the wells 18 so as to distort their color or the relative intensity of the illumination they receive.

The method of the invention for optically examining the contents of the wells of a microtiter plate having an array of wells includes the step of placing the microtiter plate on a light emitting surface having an array of regions of reduced light emission, the array of such regions being selected to be alignable with a selected portion of the array of wells of the microtiter plate. The microtiter plate is then aligned with the array of regions of reduced light emission so that the wells are observable against a dark background provided by the regions of reduced light emission while the contents of the well are illuminated by light from the light emitting surface impinging upon the wells from a generally sideward direction.

Preferably the method of the invention further includes moving the relative location of the microtiter plate wells and the array of regions of reduced light emission until the wells have been moved over a portion of the light emitting surface unobstructed by regions of reduced light emission with the contents of the wells consequently observable against a light background. Preferably the array of regions of reduced light emission is a black dot array and specifically such an array marked on a transparent overlay, such as the black dot array 33 and transparent overlay 30 described above. With the transparent overlay 30 sandwiched between the light emitting surface 26 and the microtiter plate 14 being read, the microtiter plate may be held in fixed relation to the light emitting surface and the transparent overlay moved in order to move the relative location of the array of regions of reduced light emission and the wells.

The method of the invention may further include marking selected portions of the array of wells with visually perceivable indicia located on the light emitting surface. When the light emitting surface includes a translucent plate 58 having indicator holes 56, as described above, the step of marking selected portions of the array of wells may include illuminating selected indicator light holes.

Light transmitting parts of the microtiter plate reader 10 of the invention disclosed above may all be manufactured from suitable plastics, glass, or the like by conventional means of forming such materials. The light emitting surface 26 may be illuminated from beneath by any conventional, electrical form of illumination. However, it is understood that the present invention is not limited to the particular construction and arrangement of parts illustrated and disclosed above, but embraces all such modified forms thereof as come within the scope of the following claims. Similarly, other steps than those disclosed above may be taken to perform the method of the invention, which embraces all such modified forms thereof as come within the scope of the following claims.

What is claimed is:

1. A microtiter plate reader for optically examining the contents of the wells of a microtiter plate having an array of wells, comprising:
   (a) supporting means for supporting the microtiter plate with the wells opening generally upwardly;
   (b) a light emitting surface extending under a microtiter plate when held by the supporting means to transmit light upwardly to the plate;
   (c) an array of regions of reduced light emission on the light emitting surface corresponding in relative position to a selected portion of the array of microtiter plate wells when held by the supporting means, wherein the array of regions of reduced light emission is a selected number of black dots arranged as a black dot array, each black dot generally corresponding in location to a well; and
   (d) locator means for locating the microtiter plate in selected relation to the black dot array of regions of reduced light emission such that the array of black dots can be selectively aligned or disaligned with the wells of the plate.

2. The microtiter plate reader of claim 1 wherein the supporting means is generally planar and is composed of a translucent plate lit from beneath and also defines the light emitting surface.

3. A microtiter plate reader for optically examining the contents of the wells of a microtiter plate having an array of wells, comprising:
   (a) supporting means for supporting the microtiter plate with the wells opening generally upwardly;
   (b) a light emitting surface extending under a microtiter plate when held by the supporting means;
   (c) an array of regions of reduced light emission on the light emitting surface corresponding in relative position to a selected portion of the array of microtiter plate wells when held by the supporting means; and
   (d) locator means for locating the microtiter plate in selected relation to the array of regions of reduced light emission to selectively align the wells therewith,
wherein the locator means includes a bezel located over the light emitting surface, the bezel including a window having opposing sides, a top, and a bottom and having a size sufficiently large to contain a microtiter plate to be read, whereby the microtiter plate may be located in easily maintained relation to the array of regions of reduced light emission by moving the microtiter plate snugly against a selected window side and the bottom of the window.

4. The microtiter plate reader of claim 3 including a transparent overlay that is sandwiched between the light emitting surface and the bezel, and wherein the regions of reduced light emission are black dots arrayed upon the transparent overlay.

5. The microtiter plate reader of claim 4 wherein the transparent overlay is sandwiched between the light emitting surface and the bezel in sliding relation thereto, so that the black dot array may be shifted relative to the location of the wells of a microtiter plate held within the window.

6. The microtiter plate reader of claim 5 wherein guide pins extend upwardly from the light emitting surface and the transparent overlay includes guide slots adapted to receive the guide pins in sliding relation, and having a length such that the transparent overlay may be shifted between at least two positions: a first position in which the black dot array is substantially aligned with a selected portion of the wells of a microtiter plate held within the window so that the black dots are located directly beneath the wells, and a second position in which the black dot array is offset with respect to a selected portion of the wells of the microtiter plate so that the black dots are moved from beneath the wells to leave the wells located over a portion of the light emitting surface unobstructed by black dots.

7. A microtiter plate reader for optically examining the contents of the wells of a microtiter plate having an array of wells, comprising:
  (a) supporting means for supporting the microtiter plate with the wells opening generally upwardly,
  (b) a light emitting surface extending under a microtiter plate when held by the supporting means;
  (c) an array of regions of reduced light emission on the light emitting surface corresponding in relative position to a selected portion of the array of microtiter plate wells when held by the supporting means; and
  (d) locator means for locating the microtiter plate in selected relation to the array of regions of reduced light emission to selectively align the wells therewith; and
 wherein the light emitting surface is marked with visually perceivable indicia corresponding to a selected portion of the array of wells of a microtiter plate being read.

8. A microtiter plate reader for optically examining the contents of the wells of a microtiter plate having an array of wells, comprising:
  (a) supporting means for supporting the microtiter plate with the wells opening generally upwardly,
  (b) a light emitting surface extending under a microtiter plate when held by the supporting means;
  (c) an array of regions of reduced light emission on the light emitting surface corresponding in relative position to a selected portion of the array of microtiter plate wells when held by the supporting means; and
  (d) locator means for locating the microtiter plate in selected relation to the array of regions of reduced light emission to selectively align the wells therewith;
 wherein the supporting means is generally planar and is composed of a translucent plate lit from beneath and also defines the light emitting surface; and
 wherein the the translucent plate has indicator light holes extending therethrough and arrayed thereon in a selected pattern, and including illuminating means for illuminating selected indicator light holes to mark the light emitting surface with visually perceivable indicia corresponding to a selected portion of the array of wells of a microtiter plate being read.

9. A method for optically examining the contents of the wells of a microtiter plate having an array of wells comprising the steps of:
  (a) placing the microtiter plate on a light emitting surface which transmits light upwardly to the plate, the light emitting surface having an array of regions of reduced light emission, wherein the array of regions of reduced light emission is a selected number of black dots arranged as a black dot array, each black dot generally corresponding in location to a well, the microtiter plate being placed on the light emitting surface such that the black dot array is disaligned with the bottoms of the wells of the microtiter plate so that light is transmitted directly upwardly to the bottoms of the wells; and
  (b) aligning the microtiter plate with the array of regions of reduced light emission so that the wells are over the black dots and observable against the dark background provided by the black dot regions of reduced light emission while the contents of the wells are illuminated by light from the light emitting surface impinging on the wells from a generally sideward direction.

10. A method for optically examining the contents of the wells of a microtiter plate having an array of wells comprising the steps of:
  (a) placing the microtiter plate on a light emitting surface having an array of regions of reduced light emission, the array of such regions being alignable with a selected portion of the array of wells of the microtiter plate to provide a dark background behind the wells; and
  (b) aligning the microtiter plate with the array of regions of reduced light emission so that the wells are observable against the dark background provided by the regions of reduced light emission while the contents of the wells are illuminated by light from the light emitting surface impinging on the wells from a generally sideward direction; and
 further including the step of moving the microtiter plate wells relative to the array of regions of reduced light emission until the wells have been moved so as to be over a portion of the light emitting surface unobstructed by regions of reduced light emission, with the contents of the wells consequently observable against a light background.

11. The method of claim 10 wherein the step of moving the microtiter plate wells relative to the array of regions of reduced light emission includes holding the microtiter plate in a fixed location and moving thereunder a transparent overlay that is sandwiched between the light emitting surface and the microtiter plate being read, the regions of reduced light emission including black dots arrayed upon the transparent overlay.

12. A method for optically examining the contents of the wells of a microtiter plate having an array of wells comprising the steps of:
  (a) placing the microtiter plate on a light emitting surface having an array of regions of reduced light emission, the array of such regions being alignable with a selected portion of the array of wells of the microtiter plate to provide a dark background behind the wells; and
  (b) aligning the microtiter plate with the array of regions of reduced light emission so that the wells are observable against the dark background provided by the regions of reduced light emission while the contents of the wells are illuminated by light from the light emitting surface impinging on the wells from a generally sideward direction; and
 including the step of marking a selected portion of the array of wells of the microtiter plate being read by means of visually perceivable indicia formed on the light emitting surface.

13. The method of claim 12 wherein the light emitting surface includes a translucent plate having indicator light holes extending therethrough and arrayed thereon in a selected pattern, whereupon the step of marking a selected portion of the array of wells with visually perceivable indicia includes illuminating indicator light holes selected to correspond in location to the portion of the array of wells to be marked.

* * * * *